United States Patent

Robins et al.

[11] 4,058,659
[45] Nov. 15, 1977

[54] 6,8-DISUBSTITUTED PURINE DERIVATIVES OF 9-β-D-RIBOFURANOSYL 3',5'-CYCLIC PHOSPHATE

[75] Inventors: Roland K. Robins, Santa Ana, Calif.; Dennis A. Shuman, El Paso, Tex.; Kay H. Boswell, Mission Viejo, Calif.

[73] Assignee: ICN Pharmaceuticals, Inc., Irvine, Calif.

[21] Appl. No.: 617,856

[22] Filed: Sept. 29, 1975

Related U.S. Application Data

[63] Continuation-in-part of Ser. No. 474,923, May 31, 1974, abandoned.

[51] Int. Cl.$^2$ ..................... C07H 19/18; C07H 19/20
[52] U.S. Cl. ..................................... 536/27; 424/180; 536/28
[58] Field of Search .................... 260/211.5 R; 536/27, 536/28

[56] References Cited

U.S. PATENT DOCUMENTS

| | | | |
|---|---|---|---|
| 3,225,029 | 12/1965 | Yamaoka | 260/211.5 R |
| 3,712,885 | 1/1973 | Weimann et al. | 260/211.5 R |
| 3,872,084 | 3/1975 | Jones et al. | 260/211.5 R |
| 3,872,098 | 3/1975 | Jones et al. | 260/211.5 R |

*Primary Examiner*—Johnnie R. Brown
*Attorney, Agent, or Firm*—Kay H. Boswell

[57] ABSTRACT

Compounds of formula

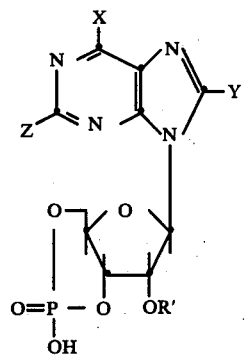

wherein X is —NR$_1$R$_2$, —Cl, —Br or SR; Y is —X, —OH or —NH$_2$; Z is hydrogen or —NH$_2$; and R' is hydrogen or C$_1$–C$_{18}$ acyl; R being hydrogen, aryl, aralkyl, substituted aryl, substituted aralkyl, or C$_1$–C$_7$ alkyl; and R$_1$ and R$_2$ being independently selected from the group consisting of hydrogen, phenyl, C$_7$–C$_{10}$ aralkyl, C$_1$–C$_7$ alkyl, C$_1$–C$_{10}$ branched chain alkyl, C$_1$–C$_7$ unsaturated alkyl or lower alkyl joined to form a 5 or 6-membered heterocyclic ring, with the proviso that when one of R$_1$ and R$_2$ are hydrogen, the other is not. The compounds variously exhibit phosphodiesterase inhibition, protein kinase activation, positive inotropic effects, adenyl cyclase inhibition and other biological activities.

17 Claims, No Drawings

6,8-DISUBSTITUTED PURINE DERIVATIVES OF 9-β-D-RIBOFURANOSYL 3',5'-CYCLIC PHOSPHATE

CROSS-REFERENCES TO RELATED APPLICATIONS

This application is a continuation-in-part of our application Ser. No. 474,923 filed May 31, 1974, and now abandoned.

BACKGROUND AND BRIEF SUMMARY OF THE INVENTION

It is known that 3',5'-cyclic purine ribonucleotides are produced in vivo in living animals, including man, and that cellular levels of certain ones of them such as cyclic guanosine monophosphate (C-GMP) and cyclic adenosine monophosphate (C-AMP) are regulated by specific phosphodiesterases. The biological activity of these cyclic nucleotides naturally follows from such in vivo production and regulation. Indeed, as reported in Sutherland, et al, "Cyclic Amp" Am. Rev. Biochem. 37, 149 (1968), cyclic AMP has now been established as an intracellular "second messenger" mediating many of the actions of a variety of different hormones.

According to the "second messenger" theory, first hormone messengers influence adenyl cyclase contained at or within cell walls to intracellularly form C-AMP from adenosine triphosphate upon receipt of the extracellular hormone signal. The formed C-AMP in turn stimulates intracellular functions particular to the target cells of the hormone. C-AMP has been shown to "activate" protein kinases which in turn occasion physiological effects such as muscle contraction, glycogenolysis, steroidogenesis and lipolysis. As a specific example of mediation of steroidogenesis by C-AMP can be mentioned cellular biosynthesis and excretion of corticosteroids as occasioned by C-AMP formed by adenyl cyclase within the cell walls of the adrenal cortex upon receipt of an extracellular signal carried by the peptide hormone ACTH.

In addition to the foregoing and as representative of the diverse roles played by C-AMP in biological processes can be mentioned implication of C-AMP as a participant in or mediator of the following metabolic reactions or pharmacologic agents: glucagon, vasopressin, lutenizing hormone, thyroid-stimulating hormone, insulin, UDPG-α-transglucosylase, phosphofructokinase, tryptophan pyrrolase, ketogenesis, amino acid uptake into liver proteins, acetate incorporation into fatty acids and cholesterol of liver, conversion lactate to glucose (gluconeogenesis), release of amylase, water and ion permeability, sugar transport, acid secretion in the gastric mucosa, platelet aggregation inhibition, catabolite repression, potentiation of antiviral activity of interferon, inhibition of HeLa and strain L cells in culture, and stimulation of antibody production (immunologic mechanism).

The so-called adrenergic effects of many hormones and drugs has now been attributed to the intracellular effects of cyclic AMP whose concentration is controlled by adenyl cyclase and cyclic nucleotide phosphodiesterase. Recent investigations have shown that at least part of the physiological effect of cyclic AMP is a result of the activation of specific protein kinases by cyclic AMP as, for example, in neurotubules isolated from the central nervous system.

Corollary to increasing recognition of the role played by this cyclic purine nucleotide has come the suggestion that it be administered in aid of lagging cellular processes. As one example can be mentioned the report that asthma may be caused by a genetic deficiency of adenyl cyclase. A consequence of such deficiency, of course, is a diminished capacity to intracellularly convert ATP to cyclic adenosine monophosphate.

Phosphodiesterase enzymes degrade purine nucleotides such as C-GMP and C-AMP. In the latter case the enzyme catalyzes hydrolysis of the 3',5'-cyclic adenosine monophosphate to 50'-adenosine monophosphate with consequent loss of function. A need has existed for cyclic purine nucleotide analogs which, while retaining the biological activity of the naturally occurring nucleotides, are resistant to degradation by phosphodiesterase. The availability of such C-AMP analogs for example, could permit maintenance of desired cyclic nucleotide monophosphate levels at dosages reduced from those requred with C-AMP itself.

The above notwithstanding, in certain cases it would appear that adenyl cyclase produces harmfully high intracellular levels of cyclic AMP. For example L. C. Chen, et. al. in The Lancet, p. 939 (May 8, 1971) demonstrates excessive cyclic AMP production by adenyl cyclase to underly the debilitating dehydration associated with cholera. Further, there is substantial evidence that the positive inotropic and chronotropic effects of catecholamines on the heart are mediated by adenyl cyclase stimulation (S. E. Epstein et al., Annals Int. Med. 72:561–568, (1970). Hence, compounds which inhibit adenylate cyclases may act to lower heart rate and be of value in the prevention of arrythmias. The finding that the mitrogen, phytohemagglutinin, stimulates the adenylate cyclase of human peripheral blood lymphocytes (J. W. Smith et al., J. Clin. Invest. 50:432–441, (1971) suggests that adenylate cyclase inhibitors might also be useful as immunosuppressive or anti-inflammatory agents.

According to this invention, there are provided compounds of the structure (a), supra, essentially all of which are superior to cyclic AMP itself from the standpoint of resistance to phosphodiesterase degradation. The compounds of the invention are themselves bioactive, or useful as intermediates in the formation of bioactive compounds, variously possessed of anti-inflammatory, anti-hypertensive, adenyl cyclase inhibitive, phosphodiesterase inhibitive and positive inotropic activity.

DESCRIPTION OF THE PREFERRED EMBODIMENTS OF THE INVENTION

A first series of the compounds of the invention is prepared by selective nucleophilic substitution of 6,8-dichloro-9-β-D-ribofuranosylpurine 3',5'-cyclic phosphate, as in Reaction Sequence I (Examples 1–7). Compound 8 is outside the scope of the invention, and was prepared simply in confirmation of the structure of Compound 5.

REACTION SEQUENCE I

Selective nucleophilic substitution of 6,8-dichloro-9-β-D-ribofuranosylpurine 3',5'-cyclic phosphate:

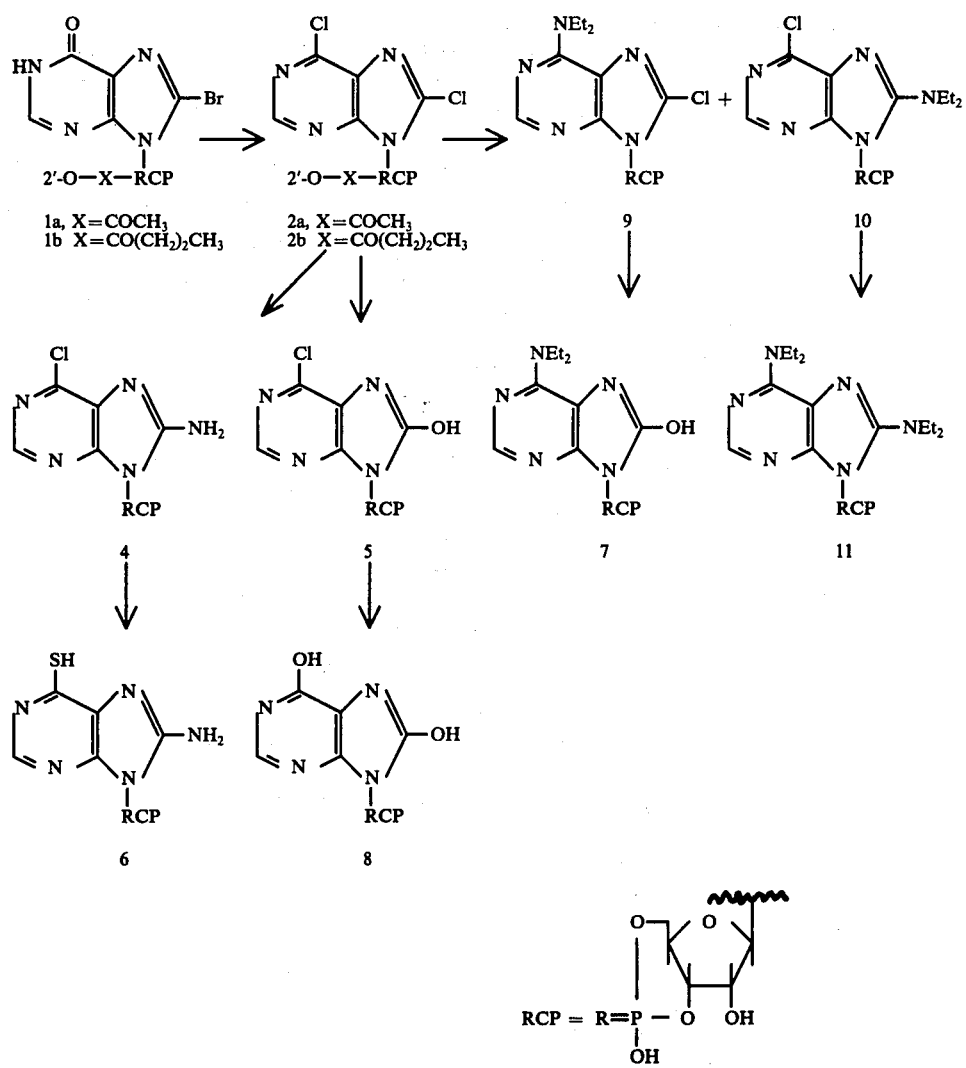

EXAMPLE 1

2′-O-Acetyl-6,8-dichloro-9-β-D-ribofuranosylpurine 3′,5′-Cyclic Phosphate (2a).

A. 2′-O-Acetyl-8-bromoinosine 3′,5′-cyclic Phosphate Triethylammonium Salt (1a).

A solution of 8-bromoinosine 3′,5′-cyclic phosphate (29 g, 71 mmol) in 10 ml triethylamine, 200 ml of dry pyridine and 150 ml of acetic anhydride was stirred overnight at room temperature. The solvent was removed in vacuo and the gum which remained crystallized upon scratching. The crude crystals were filtered off, washed off, washed with EtOAc and dissolved in a small volume of MeOH. EtOAc was added to the MeOH until solid started crystallizing out. The crystals were filtered off and dried to yield 27 g (69%) of 1a.

Anal. Calcd for $C_{18}H_{27}N_5O_8BrP$: C, 39.14; H, 4.95; N, 12.68; Br, 14.46. Found: C, 38.85; H, 4.65; N, 12.55; Br, 14.66.

B. 2′-O-Acetyl-6,8-dichloro-9-β-D-ribofuranosylpurine 3′,5′-Cyclic Phosphate Sodium Salt (2a).

A stirred mixture of 2′-O-acetyl-8-bromoinosine 3′,5′-cyclic phosphate triethylammonium salt (1a, 2 g, 3.6 mmol) in 150 ml of $POCl_3$ was placed into a 160° oil bath and refluxed for 10 min. The resulting solution was cooled and the liquid evaporated until a light oil remained. The oil was added dropwise to a mechanically stirred ice-water mixture. The resulting fine suspension was filtered and the solid washed with an ice-water mixture. The wet solid was dissolved in 25 ml of pH 5 0.5N NaOAc and extracted 3 × with 25 ml of $Et_2O$. The aqueous solution was evaporated to dryness and the residue co-distilled with EtOH until dry. The final dry residue was stirred with $CHCl_3$ and filtered. The filter cake was washed several times with $CHCl_3$ to ensure removal of product from residue salts. The filtrate and washings were evaporated to a small volume and placed onto a column of 30 g silica gel (packed in $CHCl_3$). The column was washed with 1 l. of $CHCl_3$ and then the product was eluted off with MeOH-13 $CHCl_3$ (20:80). The fractions containing product were pooled and evaporated. The residue was dissolved in a small volume of MeOH and 20 volumes of $Et_2O$ added. This suspension was evaporated, $Et_2O$ added and the suspension again evaporated to dryness to yield 300 mg (18%) of 2a.

Anal. Calcd for $C_{12}H_{10}N_4O_7Cl_2NaP.1.25$ $H_2O$: C, 30.68; H, 2.68; N, 11.93; Cl, 15.09; P, 6.59. Found: C, 30.48; H, 2,27; N, 11.64; Cl, 15.15; P, 6.57.

EXAMPLE 2

2'-O-Butyryl-6,8-dichloro-1-β-D-ribofuranosylpurine 3',5'-Cyclic Phosphate Sodium Salt (2b).

A. 8-Bromo-2'-O-butyrylinosine 3',5'-Cyclic Phosphate Triethylammonium Salt (1b).

A solution of 8-bromoinosine 3',5'-cyclic phosphate (5 g, 9.8 mmol) in MeOH containing 3 ml of triethylamine was evaporated to dryness. EtOH was added to the residue and the resulting crystals were filtered, washed with ether and dried. A solution of the dry triethylammonium salt and 4-dimethylaminopyridine (0.2 g, 1.6 mmol) in 50 ml of DMF and 30 ml of butyric anhydride was stirred for 3 hr. The solvent was evaporated and the residue was co-distilled 2 × with EtOH. The residue was dissolved in EtOH and EtOAc added until crystalls formed. The crystals were filtered, washed with EtOAc, Et₂O and dried to give 4.6 g (81%) of 1b.

B. 2'-O-Butyryl-6,8-dichloro-9-β-D-ribofuranosylpurine 3',5'-Cyclic Phosphate Sodium Salt (2b).

A solution of 8-bromo-2'-O-butyrylinosine 3',5'-cyclic phosphate triethylammonium salt (1b, 4.5 g, 9.4 mmol) was refluxed for 4 min in 30 ml of POCl₃ and worked up as for compound 2a to yield 2.65 g (56%) of 2b.

Anal. Calcd for $C_{14}H_{14}N_4O_7Cl_2NaP \cdot H_2O$: C, 34.04; H, 3.30; N, 11.40; Cl, 14.45. Found: C, 34.09; H, 3.27; N, 11.36; Cl, 14.37.

EXAMPLE 3

8-Amino-6-chloro-9-β-D-ribofuranosylpurine 3',5'-Cyclic Phosphate (4).

A solution of 2'-O-acetyl-6,8-dichloro-9-β-D-ribofuranosylpurine 3',5'-cyclic phosphate sodium salt (2a, 1g, 2.1 mmol) in 60 ml of MeOH saturated at 0° with NH₃ was stirred at room temperature overnight in a bomb. The solvent was evaporated and the residue dissolved in H₂O and placed onto a Dowex 50 (H⁺, 100–200 mesh, 5 × 30 cm) column. The column was eluted with H₂O and appropriate fractions were pooled and evaporated. MeOH was added to the residue. The solid which formed was filtered off and dried to yield 350 mg (43%) of 4. An analytical sample was obtained by recrystallization from H₂O.

Anal. Calcd for $C_{10}H_{11}N_5O_6ClP \cdot H_2O$: C, 31.46; H, 3.43; N, 18.35; Cl, 9.28. Found: C, 31.24; H, 3.58; N, 18.30; Cl, 9.31.

EXAMPLE 4

8-Amino-9-β-D-ribofuranosyl-6-thiopurine 3',5'-Cyclic Phosphate (6).

A solution of 8-amino-6-chloro-9-β-D-ribofuranosylpurine 3',5'-cyclic phosphate (4, 600 mg, 1.6 mmol), thiourea (300 mg, 4.7 mmol) and 5 drops formic acid in 20 ml of H₂O was refluxed for 1 hr. The solution was cooled to room temperature and the solid which had precipitated was filtered, washed with H₂O and dried to give 447 mg (78%) of crude 6. An analytical sample was obtained by acidifying a basic solution of the crude product with N HCl to pH 2. The solid was filtered, washed with H₂O and dried.

Anal. Calcd for $C_{10}H_{12}N_5OPS$: C, 3.34; N, 19.38; S, 8.87. Found: C, 33.26; H, 3.36; N, 19.13; S, 8.78.

EXAMPLE 5

6-Chloro-8-hydroxy-9-β-D-ribofuranosylpurine 3',5'-Cyclic Phosphate Sodium Salt (5).

A solution of 2'-O-acetyl-6,8-dichloro-9-β-D-ribofuranosylpurine 3',5'-cyclic phosphate sodium salt (2a, 1g, 2.1 mmol) in 20 ml of 1 N NaOH was stirred at room temperature overnight. A small amount of solid was filtered off and the filtrate was passed through a Dowex 50 (H⁺, 100–200 mesh, 4 × 10 cm) column. The column was washed with H₂O and the appropriate fractions were evaporated to dryness. The residue was dissloved in H₂O and passed through a Dowex 50 (Na⁺, 100–200 mesh, 4 × 5 cm) column. The column was washed with H₂O and the appropriate fractions were evaporated to dryness. The residue was co-distilled with abolute EtOH. The final dry residue was dissolved in MeOH and 4 g of silica gel added. The solvent was evaporated and the dry powder applied to a 20 g column of silica gel (packed in CHCl₃). The column was eluted with MeOH-CHCl₃ (20:80). Appropriate fractions were pooled, evaporated and the resulting residue dissolved in MeOH. Addition of ether to the MeOH precipitated 319 mg (33%) of 5.

Anal. Calcd for $C_{10}H_9N_4O_7ClNaP \cdot 3\frac{1}{2}H_2O$: C, 26.70; H, 3.58; N, 12.46. Found: C, 26.69; H, 3.26; N, 12.40.

EXAMPLE 6

6,8-Bis-(diethylamino)-9-β-D-ribofuranosylpurine 3',5'-Cyclic Phosphate (11) and 8-Chloro-6-(diethylamino)-9-β-D-ribofuranosylpurine 3',5'-Cyclic Phosphate (9).

A solution of 2'-O-acetyl-6,8-dichloro-9-β-D-ribofuranosylpurine 3',5'-cyclic phosphate sodium salt (2a, 2 g, 4.2 mmol) in 20 ml of diethylamine and 30 ml of DMF was stirred at room temperature for 4 days. The solvent was evaporated. The residue was taken up in H₂O and after adjusting to pH 7 with N HCl the solution was placed onto a Dowex 1 × 8 (formate, 100–200 mesh, 70 ml) column. The column was washed with H₂O and then eluted with a 1.4 l. gradient of 0–4 N formic acid to elute 11 and then 9. The appropriate fractions were pooled, evaporated to dryness, co-distilled twice with MeOH and the dry residues taken up in MeOH and 20 volumes of Et₂O added. The solids which formed were collected on a filter, washed with Et₂O and dried to give 0.538 g (28%) of 11 and 0.661 g (35%) of 9.

Anal. Calcd for $C_{18}H_{29}N_6O_6P$: C, 47.36; H, 6.40; N, 18.41. Found: C, 47.17; H, 6.32; N, 18.21.

Anal. Calcd for $C_{14}H_{19}N_5O_6ClP$: C, 40.05; H, 4.56; N, 16.68; Cl, 8.44. Found: C, 39.77; H, 4.51; N, 16.45; Cl, 8.52.

EXAMPLE 7

6-Chloro-8-(diethylamino)-9-β-D-ribofuranosylpurine 3',5'-Cyclic Phosphate (10).

A solution of 2'-O-butyryl-6,8-dichloro-9-β-D-ribofuranosylpurine 3',5'-cyclic phosphate sodium salt (2b, 0.5 g, 1.05 mmol) in 10 ml of diethylamine and 20 ml of DMF was stirred at room temperaturefor 1 hr. The solvent was evaporated and the residue dissolved in 50 ml of 2 N Nh₄OH. After stirring for 1 hr at room temperature, the solvent was evaporated and the residue chromatographed on a Dowex 1 (35 ml) column as for compound 9 to yield 11 (<3% by uv), 173 mg of 9 (41%) and 176 mg of 10 (40%).

Anal. Calcd for $C_{14}H_{19}N_5O_6ClP$: C, 40.05; H, 4.56; N, 16.68. Found: C, 40.25; H, 4.63; N, 16.42.

Reaction Sequence II illustrates an avenue to further 6,8-disubstituted compounds of the invention involving nucleophilic substitution of 6-chloro-8-substituted-9-β-D-ribofuranosylpurine 3′,5′-cyclic phosphates. (See followng Examples 8-33.)

REACTION SEQUENCE II

Nucleophilic substitution of 6-chloro-8-substituted-9-βD-ribofuranosylpurine 3′,5′-cyclic phosphates obtained by chlorination of 8-substituted inosine 3′,5′-cyclic phosphates:

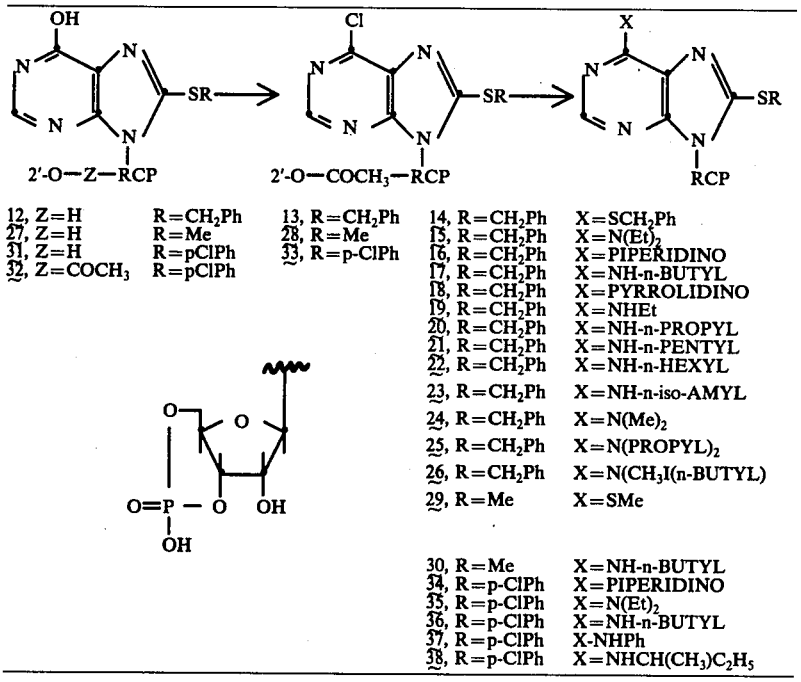

| | | |
|---|---|---|
| 12, Z=H | R=CH₂Ph | 13, R=CH₂Ph | 14, R=CH₂Ph | X=SCH₂Ph |
| 27, Z=H | R=Me | 28, R=Me | 15, R=CH₂Ph | X=N(Et)₂ |
| 31, Z=H | R=pClPh | 33, R=p-ClPh | 16, R=CH₂Ph | X=PIPERIDINO |
| 32, Z=COCH₃ | R=pClPh | | 17, R=CH₂Ph | X=NH-n-BUTYL |
| | | | 18, R=CH₂Ph | X=PYRROLIDINO |
| | | | 19, R=CH₂Ph | X=NHEt |
| | | | 20, R=CH₂Ph | X=NH-n-PROPYL |
| | | | 21, R=CH₂Ph | X=NH-n-PENTYL |
| | | | 22, R=CH₂Ph | X=NH-n-HEXYL |
| | | | 23, R=CH₂Ph | X=NH-n-iso-AMYL |
| | | | 24, R=CH₂Ph | X=N(Me)₂ |
| | | | 25, R=CH₂Ph | X=N(PROPYL)₂ |
| | | | 26, R=CH₂Ph | X=N(CH₃I(n-BUTYL) |
| | | | 29, R=Me | X=SMe |
| | | | 30, R=Me | X=NH-n-BUTYL |
| | | | 34, R=p-ClPh | X=PIPERIDINO |
| | | | 35, R=p-ClPh | X=N(Et)₂ |
| | | | 36, R=p-ClPh | X=NH-n-BUTYL |
| | | | 37, R=p-ClPh | X-NHPh |
| | | | 38, R=p-ClPh | X=NHCH(CH₃)C₂H₅ |

EXAMPLE 8

2′-O-Acetyl-8-(benzylthio)-6-chloro-9-β-D-ribofuranosylpurine 3′,5′-Cyclic Phosphate Sodium Salt (13).

METHOD A. A solution of 8-(benzylthio)inosine 3′,5′-cyclic phosphate [J. P. Miller et al, Biochemistry, 12, 5310 (1973)] (12, 5 g, 11.1 mmol) in 10% aqueous triethylamine was evaporated to dryness. The residue was co-distilled twice with pyridine. The final residue was stirred in 250 ml of pyridine with 150 ml of acetic anhydride overnight. The resulting solution was evaporated to dryness and the residue co-distilled with ethanol until all traces of pyridine were removed. 50 ml of POCl₃ were added to the residue and after refluxing for 10 min, the reaction was worked up as for compound 2a to yield 3.2 g (51%) of 13.

METHOD B. To a solution of 2′-O-acetyl-6,8-dichloro-9-β-D-ribofuranosylpurine 3′,5′-cyclic phosphate sodium salt (2a, 1 g, 2.1 mmol) in 25 ml of pH 8.7 0.1M NaOAc was added 20 drops of benzylmercaptan in 20 ml of EtOH. The solution was stirred at room temperature overnight. The solvent was evaporated and residue dissolved in 10 ml of CHCl₃. This was applied to a column (2.5 cm) of 25 g of silica gel (packed in CHCl₃). The column was washed with CHCl₃ to remove excess benzylmercaptan. The product was then eluted off with MeOH-CHCl₃ (20:80). The solvent was evaporated, the residue dissolved in EtOH and 20 volumes of Et₂O added. The precipitate was filtered off, washed with ether and dried to give 612 mg (51%) of 13.

Anal. Calcd for $C_{19}H_{17}N_4O_7ClNaPS.2H_2O$: C, 39.97; H, 3.70; N, 9.81. Found: C, 39.94; H, 3.36; N, 9.92.

EXAMPLE 9

6,8-Bis-(benzylthio)-9-D-ribofuranosylpurine 3′,5′-Cyclic Phosphate Sodium Salt (14).

A solution of 2′-O-acetyl-8-benzylthio-6-chloro-9-β-D-ribofuranosylpurine 3′,5′-cyclic phosphate sodium salt (13, 750 mg, 1.3 mmol) and 2 ml benzylmercaptan in 30 ml of 0.25 M NaOAc was refluxed overnight. The solvent was evaporated and the residue co-distilled with EtOH until dry. The dry residue was dissolved in MeOH and 4 g of silica gel added. The MeOH was evaporated and the residue applied to a column (2.5 cm) of 15 g silica gel (packed in CHCl₃). The column was eluted with CHCl₃ to remove the contaminating benzylmercaptan followed by MeOH-CHCl₃ 500 ml each of (5:95 and 10:90) then (15:85) until the product was eluted off. The fractions containing the product were pooled and the solvent evaporated. A portion of residue was taken up in EtOH, 20 volumes of Et₂O added and the solid filtered off and dried to give 80 mg of crude 2′-O-acetyl-6,8-bis-(benzylthio)-9-β-D-ribofuranosylpurine 3′,5′-cyclic phosphate sodium salt. The remainder of the residue was taken up in 20 ml of 2 N NH₄OH and let stand at room temperature for 2 hr. The solvent was evaporated and the residue co-distilled once with H₂O to ensure complete removal of NH₃. The final residue was taken up in 50 ml of EtOH-H₂O (1:1) and 50 ml of a saturated NaCl solution was added. The resulting gel was filtered off, washed well with H₂O and then with ethanol. The final gel was dried under vacuum for 12 hr at 100° to yield 290 mg (38%) of 14.

Anal. Calcd for $C_{24}H_{22}N_4O_6NaPS_2.1/2H_2O$: C, 48.84; H, 3.90; N, 9.50; S, 10.87. Found: C, 48.71; H, 4.03; N, 9.53; S, 10.79.

EXAMPLE 10

8-(Benzylthio)-6-(diethylamino)-9-β-D-ribofuranosylpurine 3',5'-Cyclic Phosphate (15).

A solution of 2'-O-acetyl-8-(benzylthio)-6-chloro-9-β-D-ribofuranosylpurine 3',5'-cyclic phosphate sodium salt (13, 3.5 g, 6.1 mmol) in 90 ml of 20% aqueous diethylamine was stirred overnight at room temperature. The solvent was evaporated and the residue was triturated 2 X with ether. The final residue was dissolved in $H_2O$ and placed onto a Dowex 50 [H+, 100–200 mesh, 2.5 × 10 cm, prewashed with $MeOH-H_2O$ (1:1)] column. The column was washed with $H_2O$ followed by 100 ml of $MeOH-H_2O$ (20:80), 100 ml $MeOH—H_2O$ (1:1) and finally $MeOH:H_2O$ (75:25) until all product was eluted. The appropriate fractions were pooled and taken to dryness. The residue was dissolved in boiling EtOH and 5 volumes $H_2O$ were added. The solution was boiled down to 1/5 volume. The crystals, which deposited upon cooling, were filtered off and dried to yield 2.4 g (75%) of 15.

Anal. Calcd for $C_{21}H_{26}N_5O_6PS.H_2O$: C, 47.99; H, 5.37; N, 13.32; S, 6.10. Found: C, 47.71; H, 5.52; N, 13.12; S, 6.08.

EXAMPLE 11

8-(Benzylthio)-6-piperidino-9-β-D-ribofuranosylpurine 3',5'-Cyclic Phosphate (16).

A solution of 2'-O-acetyl-8-(benzylthio)-6-chloro-9-β-D-ribofuranosylpurine 3',5'-cyclic phosphate sodium salt (13, 1.3 g, 2.3 mmol) in 20 ml of $H_2O$ and 10 ml of piperidine was treated as for compound 15. The residue from the column was crystalized from $H_2O$ yielding 700 mg (59%) of 16.

Anal. Calcd for $C_{22}H_{26}N_5O_6PS$: C, 50.86; H, 5.04; N, 13.48; S, 6.17. Found: C, 51.01; H, 5.11; N, 13.52; S, 6.05.

EXAMPLE 12

8-(Benzylthio)-6-(n-butylamino)-9-β-D-ribofuranosylpurine 3',5'-Cyclic Phosphate (17).

A solution of 2'-O-acetyl-8-(benzylthio)-6-chloro-9-β-D-ribofuranosylpurine 3',5'-cyclic phosphate sodium salt (13, 3.5 g, 5.25 mmol) in 50 ml of $H_2O$ and 10 ml of n-butylamine was stirred overnight at room temperature. The solvent was evaporated and the residue triturated 2 X with ether, dissolved in $H_2O$ and acidified to pH 1 with N HCl. The crude solid was filtered and then dissolved in EtOH. 5 volumes of ether were added to the EtOH and the precipitated solid collected. Recrystallization from $EtOH-H_2O$ (1:1) yield 1.68 g (61%) of 17.

Anal. Calcd for $C_{21}H_{26}N_5OPS.H_2O$: C, 47.99; H, 5.32; N, 13.32; S, 6.10. Found: C, 47.77; H, 5.48; N, 13.24; S, 6.30.

EXAMPLE 13

8-(Benzylthio)-6-pyrrolidino-9-β-D-ribofuranosylpurine 3',5'-Cyclic Phosphate (18).

A solution of 2'-O-acetyl-8-(benzylthio)-6-chloro-9-β-D-ribofuranosylpurine 3',5'-cyclic phosphate (13, 2 g, 3.5 mmol) in 20 ml of $H_2O$ containing 5 ml pyrrolidine was treated as for compound 15. $H_2O$ was added to the residue from the column and the resulting crystals were filtered off and dried to give 947 mg (51%) of 18.

Anal. Calcd for $C_{21}H_{24}N_5O_6PS.1.5H_2O$: C, 47.36; H, 5.11; N, 13.15. Found: C, 47.05; H, 5.26; N, 12.94.

EXAMPLE 14

8-(Benzylthio)-6-(ethylamino)-9-β-D-ribofuranosylpurine 3',5'-Cyclic Phosphate (19).

A solution of 2'-O-acetyl-8-(benzylthio)-6-chloro-9-β-D-ribofuranosylpurine 3',5'-cyclic phosphate sodium salt (13, 5 g, 8.8 mmol) in 60 ml of 35% aqueous ethylamine was stirred for 2 days at room temperature. The solvent was evaporated and the residue dissolved in $H_2O$ and acidified to pH 2 with 1 N HCl. The liquid was decanted off the gum which formed. After trituration with hot water, the gum solidified. The solid was filtered off, washed with water, boiling EtOH and dried to yield 2.4 g (56%) of 19. A sample was recrystallized from $EtOH-H_2O$ (1:1) for analysis.

Anal. Calcd for $C_{19}H_{22}N_5O_6PS.3/4H_2O$: C, 46.29; H, 4.76; N, 14.20; S, 6.50. Found: C, 46.23; H, 4.73; N, 14.08; S, 6.63.

EXAMPLE 15

8-(Benzylthio)-6-n-propylamino-9-β-D-ribofuranosylpurine 3',5'-Cyclic Phosphate (20).

300 mg of 13 was stirred overnight in 5 ml n-propylamine and 20 ml $H_2O$. The resulting solution was evaporated and the residue was triturated 2 X with $Et_2O$, dissolved in $H_2O$ and acidified to pH 1 with 2 N HCl. The resulting solid was filtered, washed with $H_2O$, EtOH, $Et_2O$ and dried to give 205 mg of 20.

Anal. Calcd for $C_{20}H_{24}N_5O_6PS$: C, 48.68; H, 4.90; N, 14.19. Found: C, 48.62; H, 5.08; N, 13.98.

EXAMPLE 16

8-(Benzylthio)-6-n-pentylamino-9-β-D-ribofuranosylpurine 3',5'-Cyclic Phosphate (21).

5 g of 13 was stirred in 15 ml of n-pentylamine and 100 ml $H_2O$ as per Example 12 to yield 3.4 g of 21.

Anal. Calcd for $C_{22}H_{28}N_5O_6PS.H_2O$: C, 48.97; H, 5.61; N, 12.98. Found: C, 48.94; H, 5.54; N, 12.83.

EXAMPLE 17

8-(Benzylthio)-6-n-hexylamino-9-β-D-ribofuranosylpurine 3',5'-Cyclic Phosphate (22).

5 g of 13 was stirred in 15 ml n-hexylamine and 100 ml $H_2O$ overnight. The solvent was evaporated and the residue triturated 3 X with $Et_2O$. The remaining gum was dissolved in $H_2O$/methylcellosolve and acidified to pH 1 with 2 N HCl to yield 1.61 of 22 in 3 crops. A small sample was recrystallized from $EtOH/H_2O$ for analysis.

Anal. Calcd for $C_{23}H_{30}N_5O_6PS.1/4H_2O$: C, 50.32; H, 5.79; N, 13.19. Found: C, 50.29; H, 5.99; N, 12.80.

EXAMPLE 18

8-(Benzylthio)-6-(3-methylbutylamino)-9-β-D-ribofuranosylpurine 3',5'-Cyclic Phosphate (23).

2 g of 13 was reacted with 5 ml iso-amylamine in 20 ml $H_2O$ as per Example 12 to yield 1.3 g of 23.

Anal. Calcd for $C_{22}H_{28}N_5O_6PS.1 1/4H_2O$: C, 48.57; H, 5.65; N, 12.87. Found: C, 48.57; H, 5.73; N, 12.80.

EXAMPLE 19

8-(Benzylthio)-6-dimethylamino-9-β-D-ribofuranosylpurine 3',5'-Cyclic Phosphate (24).

4 g of 13 was reacted with dimethylamine as per Example 12 to yield 2.1 g of 24.

Anal. Calcd for $C_{19}H_{22}N_5O_6PS$: C, 47.59; H, 4.62; N, 14.60. Found: C, 47.39; H, 4.71; N, 14.48.

EXAMPLE 20

8-(Benzylthio)-6-bis(n-propyl)amino-9-β-D-ribofuranosylpurine 3',5'-Cyclic Phosphate (25).

4 g of 13 was rected with dipropylamine as per Example 12 to yield 2.06 g of 25.

Anal. Calcd for $C_{23}H_{30}N_5O_6PS \cdot H_2O$: C, 49.90; H, 5.82; N, 12.65. Found: C, 49.93; H, 5.51; N, 12.72.

EXAMPLE 21

8-(Benzylthio)-6-(n-butylmethylamino)-9-β-D-ribofuranosylpurine 3',5'-Cyclic Phosphate (26).

4 g of 13 was reacted with n-butylmethylamine as per Example 12 to yield 2 g of 26.

Anal. Calcd for $C_{22}H_{28}N_5O_6PS$: C, 50.66; H, 5.41; N, 13.42. Found: C, 49.99; H, 5.52; N, 13.45.

EXAMPLE 22

6.8-Bis-(methylthio)-9-β-D-ribofuranosylpurine 3',5'-Cyclic Phosphate Sodium Salt (29).

8-Methylthioinosine 3',5'-cyclic phosphate [J. P. Miller et al, Biochemistry, 12, 5310 (1973)] 27, 2 g, 5.3 mmol) was treated as for Compound 13 up to and including the addition of the oil to the ice-water mixture. The resulting solid which formed was filtered, washed with ice-water, and then dissolved in 50 ml of pH 7 1M NaOAc. The pH of the solution was adjusted to pH 9 with 2N NaOH and 10 ml of methylmercaptan added. The reaction mixture was stirred for 3 days at 50° under a condenser. After cooling to room temperature the volume was evaporated to ¼. The solid which separated out was filtered and dissolved in 30 ml of hot $H_2O$. 30 ml of EtOH was added. Upon cooling 29 separated. 29 was filtered, washed with EtOH and dried, yielding 300 mg (12%).

Anal. Calcd for $C_{12}H_{14}N_4O_6NaPh_2 \cdot H_2O$: C, 32.28; H, 3.58; N, 12.55. Found: C, 32,07; H, 3.98; N, 12.21.

EXAMPLE 23

2'-O-Butyryl-8-(methylthio)-inosine 3',5'-Cyclic Phosphate (27).

8-methylthioinosine 3',5'-cyclic phosphate (J. P. Miller et al, Biochemistry, 12, 5310 (1973) (15 g) was treated as per Example 2-A, compound 1b, up to and including co-distillation with EtOH to yield 27 as a syrup.

EXAMPLE 24

2'-O-Butyryl-6-chloro-8-(methylthio)-9-β-D-ribofuranosylpurine 3',5'- Cyclic Phosphate Sodium Salt (28).

The product from Example 23 was treated as per Example 2-B to yield 9.3 g of 28.

EXAMPLE 25

6-n-Butylamino-8-(methylthio)-9-β-D-ribofuranosylpurine 3',5'-Cyclic Phosphate (30).

7.7 g of 28 was reacted with 5 ml n-butylamine and 30 ml $H_2O$ as per Example 12 yield 3.9 g of 30.

Anal, Calcd for $C_{15}H_{22}N_5O_6PS \cdot H_2O$: C, 40.08; H, 5.38; N, 15.58. Found: C, 40.13; H, 5.27; N, 15.74.

EXAMPLE 26

2'-O-Acetyl-8-(p-chlorophenylthio)inosine 3',5'-Cyclic Phosphate (32).

8-(p-Chlorophenylthio)inosine 3',5'-cyclic phosphate [J. P. Miller et al, Biochemistry, 12, 5310 (1973)](31, 6.0 g, 12.2 mmol) was dissolved in MeOH containing 3 ml of triethylamine. The solution was evaporated to dryness and the residue was dissolved in a mixture of DMF (100 ml) and acetic anhydride (50 ml) containing 4-dimethylaminopyridine (305 mg, 2.5 mmol). The solution was stirred for 2 hr. at room temperature, the solvent was evaporated and the residue dissolved in a minimum volume of MeOH-$H_2O$ (1:1). This was passed through a Dowex 50 [H+, 100-200 mesh, 4.5 × -cm, prewashed with MeOH-$H_2O$ (1:1)]column. The eluate was evaporated to a small volume and the crystals which formed were filtered off and washed with $H_2O$. Recrystallization from $H_2O$ yielded 5.43 g (86%) of 32 in two crops.

Anal. Calcd for $C_{18}H_{16}N_4O_8ClPS$: C, 41.99; H, 3.13; N, 10.88. Found: C, 41.79; H, 3.36; N, 10.75.

EXAMPLE 27

2'-O-Acetyl-6-chloro-8-(p-chlorophenylthio)-9-β-D-ribofuranosylpurine 3',5'-Cyclic Phosphate Sodium Salt (33).

To 2'-O-acetyl-8-(p-chlorophenylthio)inosine 3',5'-cyclic phosphate (32, 1.9 g, 3.7 mmol) and 2,6-lutidine (394 mg, 3.7 mmol) was added 30 ml of $POCl_3$. The mixture was placed in a 160° oil bath and, after refluxing for 4 min., the reaction worked up as for compound 2a to yield 822 mg (40%) of 33.

Anal. Calcd for $C_{18}H_{14}N_4O_7Cl_2NaPS$: C, 38.93; H, 2.54; N, 10.09. Found: C, 38,72; H, 2.52; N, 10.10.

EXAMPLE 28

8-(p-Chlorophenylthio)-6-piperidino-9-β-D-ribofuranosylpurine 3',5'-Cyclic Phosphate (34).

A solution of 2'-O-acetyl-6-chloro-8-(p-chlorophenylthio)-9-β-D-ribofuranosylpurine 3',5'-cyclic phosphate sodium salt (33, 1.0 g, 1.8 mmol) in 20 ml of $H_2O$ containing 3 ml piperidine was stirred overnight at room temperature. The solvent was evaporated and the residue was triturated 2 × with ether. The final residue was dissolved in $H_2O$ and the pH adjusted to pH 1 with N HCl. The liquid was decanted off of the gum which formed. The gum was triturated with $H_2O$ and then dissolved in hot $H_2O$. Upon cooling, a semi-solid separated out of solution, and upon standing overnight, it solidified. The solid was filtered off and dried to yield 670 mg (70%) of 34.

Anal. Calcd for $C_{21}H_{23}N_5O_6ClPS$: C, 46.71; H, 4.29; N, 12.97. Found: C, 46.55; H, 4.28; N, 12.80.

EXAMPLE 29

8-(p-Chlorophenylthio)-6-(diethylamino)-9-β-D-ribofuranosylpurine 3',5'-Cyclic Phosphate (35).

METHOD A. A solution of 2-O-acetyl-6-chloro-8-(p-chlorophenylthio)-9-β-D-ribofuranosylpurine 3',5'-cyclic phosphate sodium salt (33, 0.8 g, 1.4 mmol) in 30 ml of 20% aqueous diethylamine was treated as for compound 15. The residue from the column was dried to yield 395 mg (51%) of 35.

Anal. Calcd for $C_{20}H_{23}N_5O_6ClPS$: C, 45.15; H, 5.29; N, 13.16. Found: C, 45.29; H, 5.07; N, 13.19.

METHOD B. A solution of 8-chloro-6-(diethylamino)-9-β-D-ribofuranosylpurine 3',5'-cyclic phosphate (9, 270 mg, 0.65 mmol), sodium methoxide (200 mg, 3.7 mmol) and p-chlorobenzenethiol (300 mg, 2.1 mmol) in 50 ml of MeOH was refluxed overnight. The solvent was evaporated and the residue was triturated 2 × with ether. The final residue was dissolved in $H_2O$ and acidified to pH 1 with N HCl. The resulting solid was collected and dissolved in $H_2O$ by the difference of 2 N NaOH. The solvent was evaporated and the residue co-distilled 2 × with EtOH. The dry residue was dissolved in MeOH and 2 g silica gel was added. After evaporating the solvent, the residue was put onto a column of 10 g of silica gel (packed in $CHCl_3$). The column was washed with $CHCl_3$ to remove excess p-chlorobenzenethiol and then the product was eluted off with MeOH-$CHCl_3$ (30:70). The fractions containing the product were pooled and were evaporated to dryness to give 35 ml (9%) of 35.

Anal. Calcd for $C_{20}H_{22}N_5O_6ClNaPS\cdot 2H_2O$: C, 41.06; H, 4.44; N, 11.97. Found: C, 40.82; H, 4.27; N, 12.38.

EXAMPLE 30

6-n-Butylamino-8-(p-chlorophenylthio)-9-β-D-ribofuranosylpurine 3',5'-Cyclic Phosphate (36).

6.7 g of 33 was reacted with n-butylamine as per Example 28 to yield 5.14 g of 36.

Anal. Calcd for $C_{20}H_{23}N_5O_6ClPS\cdot H_2O$: C, 44.00; H, 4.62; N, 12.83. Found: C, 43.95; H, 4.68; N, 12.81.

EXAMPLE 31

6-Anilino-8-(p-chlorophenylthio)-9-β-D-ribofuranosylpurine 3',5'-Cylic Phosphate (37).

EtOH was added dropwise to a mixture of 33 in 20 ml $H_2O$ and 3 ml aniline until a clear solution was obtained. After stirring overnight, the solid which had separated out of solution was filtered and washed with EtOH. A second crop of solid was filtered and washed. The combined crops were dissolved in hot EtOH/$H_2O$ with the addition of 1 N $NH_4OH$. The solution was acidified to pH 1 with 2 N HCl. The resulting solid was filtered, washed and dried to yield 406 mg of 2'-O-acetyl-6-anilino-8-(p-chlorophenylthio)-9-β-D-ribofuranosylpurine 3',5'-cyclic phosphate. 150 mg of the 2'-O-acetyl intermediate was dissolved in 25 ml of 2 N $NH_4OH$ by the addition of MeOH. After stirring for 2 hr the solvent was evaporated and the residue dissolved in $H_2O$ and put onto a Dowex 50 (H+, 2 × 5 cm) column. The column was washed with $H_2O$ and the product was eluted off with 1:1 MeOH/$H_2O$. The column eluate was evaporated to yield 90 mg of 37.

Anal. Calcd for $C_{22}H_{19}N_5O_6ClPS\cdot \frac{1}{2}H_2O$: C, 45.95; H, 3.85; N, 12.18. Found: C, 45.88; H, 3.70; N, 11.96.

EXAMPLE 32

8-(p-Chlorophenylthio)-3-(1-methylbutylamino)-9-β-D-ribofuranosylpurine 3',5'-Cylic Phosphate (38).

1.3 g of 33 was reacted with 5 ml of sec-butylamine as per Example 28 up to and including acidification. The gum obtained from the pH2 solution was dissolved in a minimum volume of diluted ammonia and placed onto a Dowex 50 (H×, 2 × 5 cm) column. The column was washed with $H_2O$ and the product eluted off with 1:10 MeOH:$H_2O$. The column eluate was evaporated to yield 190 mg of 38.

Anal. Calcd for $C_{20}H_{23}N_5O_6ClPS\cdot 1\frac{1}{2}H_2O$: C, 44.73; H, 4.50; N, 13.04. Found: C, 45.06; H, 4.40; N, 12.77.

EXAMPLE 33

In a manner analogous to that shown in K. Muneyama, et al, Biochemistry, 10, 2390 (1971) the following 8-substituted (arylthio)-adenosine 3',5'-cyclic phosphates are prepared:

8-(o-Tolylthio)adenosine 3',5'-cyclic phosphate
8-(p-Methoxyphenylthio)adenosine 3',5'-cyclic phosphate
8-(p-Bromophenylthio)adenosine 3',5'-cyclic phosphate
8-(p-Methoxybenzylthio)adenosine 3',5'-cyclic phosphate
8-(p-Methylbenzylthio) adenosine 3',5'-cyclic phosphate
8-(p-Methoxybenzylthio)adenosine 3',5'-cyclic phosphate
8-(m-Nitrobenzylthio)adenosine 3',5'-cyclic phosphate
8-p-Nitrobenzylthio)adenosine 3',5'-cyclic phosphate
8-(p-Florobenzylthio)adenosine 3',5'-cyclic phosphate
8-(p-Chlorobenzylthio)adenosine 3',5'-cyclic phosphate Following the procedure of J. P. Miller, Biochemistry, 12, 5310 (1973) the adenosine 3',5'-cyclic phosphate can be converted to the corresponding inosine 3',5'-cyclic phosphate which in turn, following the procedure of Examples 26 and 27, can be converted to the corresponding 2-acyl-6-chloro-8-substitutedthio-9-βD-ribofuranosylpurine 3',5'-cyclic phosphate products. Representative compounds include:

2'-O-Acetyl-6-chloro-8-(O-tolylthio)-9-β-D-ribofuranosylpurine 3',5'-cyclic phosphate sodium salt,
2'-O-Acetyl-6-chloro-8-(p-bromophenylthio)-9-β-D-ribofuranosylpurine 3',5'-cyclic phosphate sodium salt, 2'-O-Acetyl-6-chloro-8-(p-methoxybenzylthio)-9-β-D-ribofuranosylpurine 3',5'-cyclic phosphate sodium salt, 2'-O-Acetyl-6-chloro-8-(p-methoxybenzylthio)-9-β-D-ribofuranosylpurine 3',5'-cyclic phosphate sodium salt.
2'-O-Acetyl-6-chloro-(m-nitrobenzylthio)-9-β-D-ribofuranosylpurine 3',5'-cyclic phosphate sodium salt,
2'-O-Acetyl-6-chloro-8-(p-nitrobenzylthio)-9-β-D-ribofuranosylpurine 3',5'-cyclic phosphate sodium salt,
2'-0-Acetyl-6-chloro-8-(p-florobenzylthio)-9-β-D-ribofuranosyl-purine 3',5'-cyclic phosphate sodium salt, and 2'-O-Acetyl-6-chloro-8-(p-chlorobenzylthio)-9-β-D-ribofuranosyl-purine 3', 5'-cyclic phosphate sodium salt, which are useful as intermediates as per Example 28 for preparation of other 6-substituted-8-substituted-thio-9-β-D-ribofuranosylpurine 3',5'-cyclic phosphates.

Reaction Sequence III illustrates yet a further synthetic avenue to preferred 6,8-disubstituted bioactive compounds (see following Examples 34-37).

REACTION SEQUENCE III $N^1$-alkylation of 8-substituted adenosine 3',5'-cyclic phosphates followed by Dimroth rearrangement

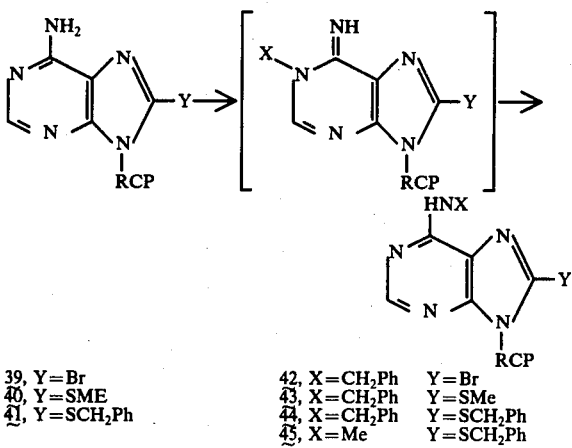

39, Y=Br
40, Y=SME
41, Y=SCH₂Ph

42, X=CH₂Ph  Y=Br
43, X=CH₂Ph  Y=SMe
44, X=CH₂Ph  Y=SCH₂Ph
45, X=Me     Y=SCH₂Ph

RCP - See Scheme I

EXAMPLE 34

6-(Benzylamino)-8-bromo-9-β-D-ribofuranosylpurine 3',5'-Cyclic Phosphate (42).

A solution of 8-bromoadenosine 3',5'-cylic phosphate [Muneyama, et al, Biochemistry, 10, 2390 (1971)] (1.22 g, 3 mmol), 1,5-diazabicyclo-[5.4.0]undecene-5 (1.0 ml, 6.0 mmol) and α-bromotoluene (0.4 ml) in 8 ml of DMSO was stirred for 18 hr. An additional aliquot of α-bromotoluene was added and the stirring was continued for 36 hr. The solution was added to 150 ml H₂O containing NaHCO₃ (1.3 g) and Na₂CO₃ (1.0 g) and heated on a steam bath for 2 hr. After adjusting the pH to 1.5 with concentrated HCl, the solution was absorbed onto a charcoal column (30 ml, Barnebey-Cheney, UU 50-200 mesh) and washed well with H₂O. The nucleotide was eluted with EtOH-NH₄OH-H₂O (4:1:5). The solvent was evaporated and the residue in a small volume of H₂O was applied to a Dowex 1 × 2 (formate, 100-200 mesh, 2.5 × 3 cm) column. The column was washed with water and then eluted with a 1 l. gradient of 0 to 4 N formic acid. The appropriate fractions were pooled and evaporated. The residue was suspended in a small amount of H₂O, filtered and air-dried to yield 142 mg (9.0%) of 42.

Anal. Calcd for $C_{17}H_{17}N_5O_6BrP\cdot 1\frac{3}{4}H_2O$: C, 38.53; H, 3.95; N, 13.21. Found: C, 38.79; H, 3.74; N, 12.92.

EXAMPLE 35

6-(Benzylamino)-8-(methylthio)-9-β-D-ribofuranosylpurine 3',5'-Cyclic Phosphate (43).

Aliquots of β-bromotoluene (0.25 ml) were added at times 0, 20 min., 40 min., 80 min., and 5 hr. to a solution at 8-(methylthio)-adenosine 3',5'-cyclic phosphate [K. Muneyama et al, Biochemistry, 10, 2390 (1971)] (1.0 g, 249 mmol) and 1,5-diazabicyclo [5.4.0]undecene-5- (812 mg, 3.2 mmol) in 5 ml DMSO at 60°. After cooling to room temperature overnight, the reaction mixture was added to 150 ml H₂O containing NaHCO₃ (1.2 g) and Na₂CO₃ (0.9 g). The solution was heated on a steam bath for 2 ½ hr. After filtering, the volume was diluted to 1 l., 10 g NaCl added and the solution extracted 2 × with 50 ml CHCl₃. The aqueous phase was applied to an amberlite XAD-4 (130 ml), 2.5 × 25 cm) column. The column was washed well with H₂O and the nucleotide eluted with a 5.1 gradient of H₂O vs MeOH. The solvent was evaporated and the residue suspended in MeOH, filtered and dried at room temperature to yield 340 mg (29%) of 43.

Anal. Calcd for $C_{18}H_{20}N_5O_6PS$: C, 46.44; H, 4.33; N, 15.04. Found: C, 46.20; H, 4.19; N, 14.77.

EXAMPLE 36

6-(Benzylamino)-8-(benzylthio)-9-β-D-ribofuranosylpurine 3',5'-Cyclic Phosphate (44).

Aliquots of β-bromotoluene (0.2 ml) were added to a solution of 8-benzylthio)adenosine 3',5'-cyclic phosphate sodium salt [K. Muneyama et al, Biochemistry, 10, 2390 (1971)] (442 mg, 1 mmol) and 1,5-diazabicyclo [5.4.0]undecene-5-(0.2 ml, 1.2 mmol) in 1 ml DMSO at times 0, 1 hr. After stirring an additional 18 hr, 50 ml H₂O was added and the resulting solution heated on a steam bath for 2 hr. After cooling, the pH was adjusted to 1.5 with HCl. The precipitate was filtered and reprecipitated from H₂O with conc HCl to yield 326 mg (66%) of 44. An analytical sample was obtained by chromatography on Dowex 1 as for compound 42.

Anal. Calcd for $C_{24}H_{24}N_5O_6PS$: C, 53.23; H, 4.46; N, 12.93. Found: C, 53.14; H, 4.46; N, 13.05.

EXAMPLE 37

8-(Benzylthio)-6-(methylamino)-9-β-D-ribofuranosylpurine 3',5'-Cyclic Phosphate (45).

A solution of 8-benzylthiodenosine 3', 5'-cyclic phosphate sodium salt [K. Muneyama et al, Bichemistry, 10, 2390 (1971)] (1.32 g, 2.7 mmol), 1.5-diazabicyclo [5.4.0]undecene-5 (0.67 ml, 4.05 mmol) and methyl iodide (0.5 ml) in 4 ml DMSO was stirred at room temperature overnight. The reaction was added to 150 ml of H₂O containing NaHCO₃ (1.3 g) and Na₂CO₃ (1.0 g) and heated on a steam bath for 3 hr. After adjusting the pH to 1.5 with conc HCl, the reaction was placed under an aspirator vaccum for 1 hr. The pH was readadjusted to 8.5 with 2 N NaOH and the solution chromatographed on Dowex 1 as for compound 31. The residue from the column was suspended in MeOH and filtered to yield 375 mg (28%) of 45. An analytical sample was obtained by dissolving a sample in a large volume of MeOH-H₂O, filtering and evaporating to dryness. THe residue was suspended in H₂O, filtered and dried.

Anal. Calcd for $C_{18}H_{20}N_5O_6PS \cdot 1 \frac{1}{2}H_2O$: C, 43.90; H, 4.70; N, 14.22. Found: C, 43.72; H, 4.36; N, 14.36

Reaction Sequence IV illustrates another variation of the synthetic avenue of Sequence III to preferred 6,8-disubstituted bioactive compounds (see following Examples 38-42).

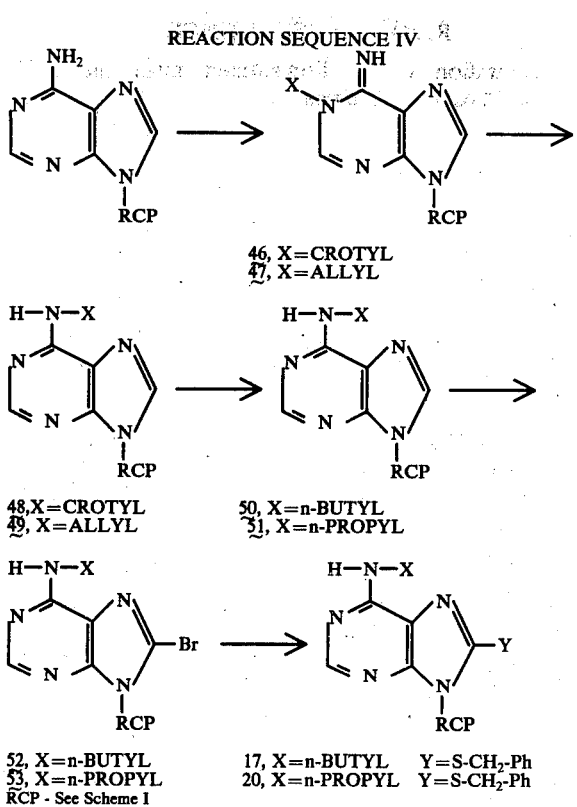

EXAMPLE 38

N¹Crotyladenosine 3',5'-Cyclic Phosphate (46).

In a 2 liter, 3 neck flask equipped with a thermometer, drying tube, and reflux condensor, a suspension of adenosine 3',5'-cyclic phosphate (230 g, 0.70 mol) and 1,5-diazabicyclo [5.4.0]undecene-5 (115 g, 0.75 mol) in 600 ml of DMF was stirred at 60° (internal temperature) until a solution was obtained. 2,6-Lutidine (37.4 g, 240 ml) was added dropwise, followed by the slow addition of crotyl bromide (135 g, 1 mol). The reaction mixture was stirred an additional 5 hr at 60°. The product which had slowly crystalized from solution was filtered, washed with a small volume each of DMF and MeOH, and dried to yield 146 g of 46.

EXAMPLE 39

N¹-Allyladenosine 3',5'-Cyclic Phosphate (47).

Adenosine 3',5'-cyclic phosphate (165 g) was treated as per Example 38 up to and including addition of allyl bromide (60 ml). After stirring at 60° overnight, the reaction mixture was filtered and washed with DMF. The resulting solid was stirred in 1 liter MeOH and 100 ml pyridine. The crystalline product was filtered, washed with MeOH, and dried to yield 86 g of 47.

EXAMPLE 40

8-(Benzylthio)-6-butylamino-9-β-D-ribofuranosylpurine 3',5'-Cylic Phosphate (17) via N¹-Crotyladenosine 3',5'-Cyclic Phosphate.

46 (140 g, 0.365 mol) was dissolved in 800 ml of 1 N NaOH and heated at 75° for 2 hr. The reaction mixture was cooled and 24 ml of glacial acetic acid added. After the addition of 4.0 gm 5% Pd on carbon, reaction mixture was shaken under $H_2$ (≈ 40 psi for 5 hr) until 87 lbs. of $H_2$ was taken up (91 lbs theoretical). The catalyst was filtered and washed with 200 ml of hot $H_2O$. To the combined filterate plus wash (1 liter) was added $Br_2$ (61 g, 21 ml, 0.38 mol) in 2 portions at 30 minute intervals. 40 g NaOAc was added and the solution was stirred at room temperature. After 4 hr, an additional 10 ml $Br_2$ was added and stirring was continued for 3 days.

The solution was purged with $N_2$ for 2 hr followed by the addition of NaBH₄ until the solution gave a negative KI-starch test. The pH was adjusted to pH 12 with 30% NaOH and 40 ml of benzylmercaptan was added. The resulting solution was heated at 70° for 1 hr and then acidified to pH 1.8 with conc. HCl. The acidic solution was stirred and allowed to slowly cool. The crude product was filtered, washed with $H_2O$ and then EtOH. The crude material was dissolved in $CHcl_3$ by the addition of triethylamine. The $CHCl_3$ solution was added to a column of 200 g of dry silica gel. The column was washed with $CHCl_3$ and the product eluted with 4% EtOH in $CHCl_3$. The appropriate column fractions were pooled and evaporated. THe triethylammonium salt was dissolved in 100 ml of warm 2 N NH₄OH, 500 ml of MeOH was addded, and the solution acidified to pH 2 with conc. HCl. After cooling the resulting solid was filtered, washed with $H_2O$ and EtOH, and dried yielding 101 g of 17 which was identical to that prepared in Example 12.

EXAMPLE 41

8-(Benzythio)-6-propylamino-9-β-D-ribofuranosylpurine 3',5'-Cyclic Phosphate (20) Via N¹-Allyladenosine 3',5'-Cyclic Phosphate.

47 (75 g) was treated as per Example 40 to yield 18 g of crude 20 before silica gel chromatography. After chromatography the material obtained was identical to that of Example 15.

EXAMPLE 42

8-Bromo-6-n-butylamino-9-β-D-ribofuranosylpurine 3',5'-Cyclic Phosphate (52).

46 (14 g) was reacted as per Example 40 up to and including purging with $N_2$. The resulting solution was percolated through a Dowex 50 (H+, 5 × 20 cm) column. The column was eluted with $H_2O$. The appropriate fractions containing the product were pooled and evaporated to yield 5.1 g of 52.

Anal. Calcd for $C_{14}H_{19}N_5O_6BrP$: C, 36.22; H, 4.12; N, 15.08. Found: C, 36.20; H, 4.12; N, 15.05.

Optionally, unsaturated compounds such as 50 and 51 need not be reduced to 52 and 53 (respectively) but may be selectively halogenated at the 8-position and further subjected to nucleophilic substitution of the 8-halogen to yield 6,8-disubstituted compounds wherein the 6-position is occupied by an unsaturated alkyl amine such as allylamino, crotylamino, propragylamino, and isopentenylamino.

While in the preferred compounds of the invention position 2 of the aglycon is unsubstituted, the methodology of the invention is equally suited to the preparation of 6,8-disubstituted analogs of guanosine 3',5'-cyclic phosphate. Reaction Sequence V includes one such preparation (that of Compound 56) wherein the methodology of Reaction Sequence I is applied, as is more fully set out in Examples 43–46 infra. Reaction Sequence V illustrates, for similar reasons, the preparation of a 6,8-substituted cyclic GMP analon (Compound 60) via nucleophilic attack on the 6-chloro substituent of preformed 2-amino-8- substituted 3',5'-cyclic phosphates (see following Examples 47–50 and compare Reaction Sequence II, infra).
REACTION SEQUENCE V
Preparation of 6,8-disubstituted guanosine 3',5'-Cyclic Phosphate Analogs
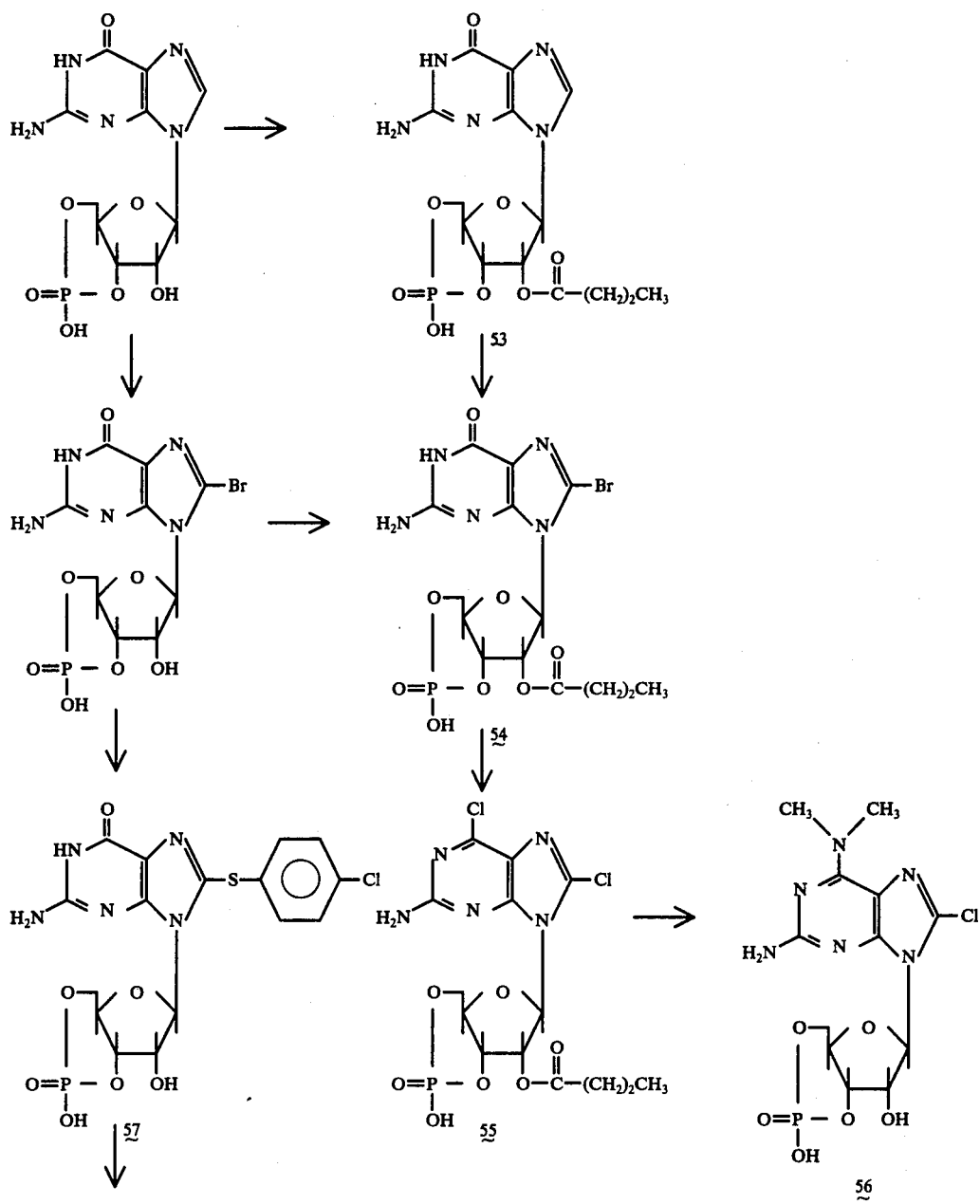

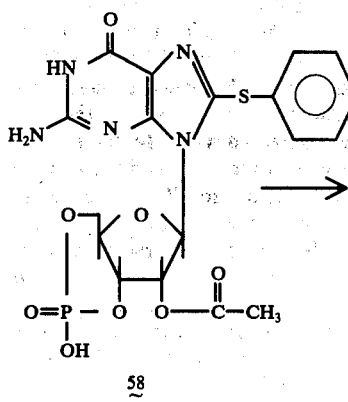 58

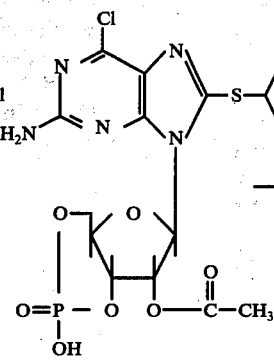 59

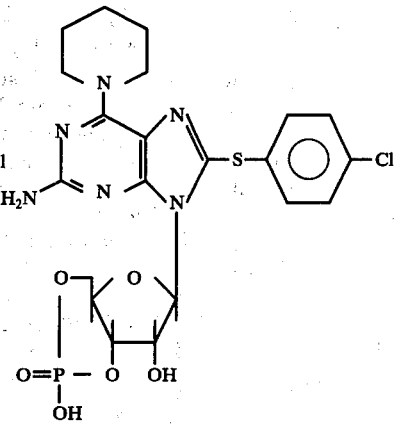 60

EXAMPLE 43

2'-O-Butyrylguanosine 3',5'-Cyclic Phosphate Sodium Salt (53).

cGMP sodium salt (2.0 g, 5.4 mmol) and 4-dimethylaminopyridine (0.15 g, 1.23 mmol) were dissolved in 50 ml of DMF and 5 ml butyric anhydride. After stirring at room temperature for 3 hrs. the reaction mixture was filtered and the filtrate evaporated to dryness. EtOH was added to the residue and the resulting solid was filtered, washed with EtOH and dried to yield 0.870 g (37%) of 53. $\lambda_{max}^{pH1}$257 nm, 282 sh ($\epsilon$ 11,800, 8,300)m $\lambda_{max}^{pH7}$253 nm, 277 sh ($\epsilon$ 13,300, 8,700), $\lambda_{max}^{pH11}$260 nm ($\epsilon$ 11,800).

Anal. Calcd for $C_{14}H_{14}N_5O_8NaP$: C, 38.45; H, 3.91; N, 16.01. Found: C, 38.35; H, 4.07; N, 15.93.

EXAMPLE 44

8-Bromo-2'-O-Butyrylguanosine 3',5'-Cyclic Phosphate Triethylammonium Salt (54).

150 Ml of bromine water (saturated at room temperature) was added dropwise over a 2 hr. period to a solution of 2'-O-butyryl cGMP Na$^{30}$, (53, 11.5 g, 26 mmol) in 500 ml of H$_2$O. The solution was stirred for an extra ½ hr. and then N$_2$ was bubbled through until the color changed from orange to light yellow. The solution was evaporated to ≈ 300 ml and was diluted with 300 ml of MeOH. This was passed through a Dowex 50 (H+, 100–200 mesh, 5 × 24 cm, prewashed with MeOH-H$_2$O [1:1]) column. The eluate was evaporated to dryness and the residue was co-distilled with EtOH until it was a dry foam. Acetone was added to the foam and the resulting solid was filtered and dried yielding 10.5 g of the crude free acid of 54. The free acid was dissolved in MeOH containing 5 ml of triethylamine. The solution was evaporated to dryness and the residue was dissolved in CHCl$_3$ and placed onto a 30 g silica gel (packed in CHCl$_3$)column. The column was washed with CHCl$_3$ and then the product was eluted off with MeOH-CHCl$_3$ (10:90). The appropriate fractions were pooled and evaporated to dryness. CHCl$_3$ was added to the residue and the resulting crystals were filtered off and dried to yield 5 g (32% of 54; $\epsilon_{max}^{pH1}$260 nm, 275 sh ($\epsilon$ 15,500, 12,800), $\epsilon_{max}^{pH11}$270 nm ($\epsilon$ 13,600).

Anal. Calcd for $C_{20}H_{32}N_6O_8BrP$: C, 40.34; H, 5.41; N, 14.11; Br, 13.42. Found: C, 40.18; H, 5.40; N, 14.06; Br, 13.45.

EXAMPLE 45

2-Amino-2'-O-Butyryl-6,8-Dichloro-9β-D-Ribofuranosylpurine 3',5'-Cyclic Phosphate (55).

To 8-bromo-2'-O-butyrylguanosine 3',5'-cyclic phosphate triethyl- ammonium salt (54, 0.7 g, 1.18 mmol) wet with 2.6-lutidine (0.17 g, 1.6 mmol) was added 50 ml of phosphoryl chloride. The mixture was refluxed for 3 min in a 160° oil bath. The resulting solution was evaporated to a light oil. The oil was added dropwise to a mechanically stirred ice-water mixture. The resulting fine suspension was filtered and the solid washed with an ice-water mixture. The wet solid was dissolved in 20 ml of pH 5.3. 1.0 M NaOAc and extracted 3 × with Et$_2$O. The solution was evaporated and the residue co-distilled with EtOH until dry. The dry residue was extracted with CHCl$_3$. The CHCl$_3$ was evaporated to a small volume and 20 volumes of Et$_2$O added to precipitate 320 mg (55%) of crude (contains ½ mol of NaOAc by elements analysis and nmr) sodium salt of 55. An analytical sample was obtained by passing a sample of the sodium salt through a Dowex 50 (H+, 100-200 mesh) column: $\lambda_{max}^{pH}$252, 311 nm ($\epsilon$ 9,700, 8,200).

Anal. Calcd for $C_{14}H_{16}N_5O_7Cl_2P$: C, 35.91; H, 3.44; N, 14.95. Found: C, 36.04; H, 3.37; N, 14.80.

EXAMPLE 46

2-Amino-8-chloro-6-dimethylamino-9-β-D-ribofuranosylpurine 3',5'-Cyclic Phosphate (56).

A solution of 2-amino-2'-O-butyryl-6,8-dichloro-9-(β-D-ribofuranosyl) purine 3',5'-cyclic phosphate sodium salt (55, 0.6 g, 1.2 mmol) in 30 ml EtOH and 2 ml dimethylamine was stirred under reflux for 1 hr. and then at room temperature overnight. The solvent was evaporated and the residue co-distilled 2 × with EtOH. The final residue in H$_2$O was placed onto a Dowex 50 (H+, 100–200 mesh, 2 × 6 cm) column. The column was eluted with H$_2$O and the appropriate fraction pooled and evaporated to dryness. After co-distilling 2 × with EtOH, the residue was suspended in EtOH, filtered, washed with Et$_2$O and dried to yield 95 mg (20%) of 56. $\lambda_{max}^{pH1}$262, 304 nm ($\epsilon$ 14,800, 13,800), $\lambda_{max}^{pH11}$230,285 nm, 272 sh ($\epsilon$ 18,200, 16,000, 13,700).

Anal. Calcd for $C_{12}H_{16}N_6O_6ClP$: C, 35.43; H, 3.96; N, 20.66; Cl, 8.71. Found: C, 35.20; H, 4.06; N, 20.44; Cl, 8.79.

EXAMPLE 47

8-(p-Chlorophenylthio)guanosine 3',5'-Cyclic Phosphate Sodium Salt (57)

An H$_2$O (25 ml)-MeOH (500 ml) suspension of 8-bromo-cGMP (10 g, 23.6 mmol), p-chlorophenylthiol (3.7 g, 25.7 mmol) and NaOAc (4 g) was refluxed for 24 hr. The opaque solution was filtered and evaporated to a solid. The solid was triturated 3 × 100 ml with hot EtOH and then dissolved in a minimum amount of hot H$_2$O. The aqueous solution was cooled and filtered to yield 8.3 g (66%) of 57: $\epsilon_{max}^{pH1}$275 nm ($\epsilon$ 21,500), $\lambda$pH 11/max 296 nm ($\epsilon$ 21,500).

Anal. Calcd for C$_{16}$H$_{13}$ClN$_5$PO$_7$SNa·1.25 H$_2$O: C, 36.18; H, 2.94; N, 13.32; S, 6.30. Found: C, 36.17; H, 2.94; N, 13.18; S, 6.03.

EXAMPLE 48

2'-O-Acetyl-2-amino-8-(p-chlorophenylthio)-guanosine 3',5'-Cyclic Phosphate (58).

H$_2$O was added dropwise to 8-(p-chlorophenylthio)-guanosine 3',5'-cyclic phosphate sodium salt (57, 3 g, 5.6 mmol) in hot (90° C) DMF until solution occurred. The solution was cooled to room temperature, 4-dimethylaminopyridine (150 mg., 1.2 mmol) and 10 ml acetic anhydride were added and the resulting solution stirred for 45 min. The solvent was evaporated and the residue in MeOH-H$_2$O (1:1) passed through a Dowex 50 (H$^+$), 100–200 mesh, 4 × 9 cm) column. The column was eluted with MeOH-H$_2$O (1:1), the eluate evaporated and the residue co-distilled with EtOH until dry yielding 2.1 g of 58.

EXAMPLE 49

2'-O-Acetyl-2-amino-6-chloro-8-(p-chlorophenylthio)-9-β-D-ribofuranosyl-purine 3',5'-Cyclic Phosphate Sodium Salt (59).

A suspension of 2'-O-acetyl-8-(p-chlorophenylthio)-guanosine 3',5'-cyclic phosphate (58, 2 g, 3.7 mmol) and 2,6-lutidine (400 mg, 3.7 mmol) in 30 ml of phosphoryl chloride was placed into a preheated 160° C oil bath and refluxed 4 min. The solution was evaporated to a small volume and added dropwise to a mechanically stirred ice-water mixture. The resulting fine suspension was filtered and the solid washed with an ice-water mixture. The solid was dissolved in 25 ml of pH 5 0.5 N NaOAc and extracted 3 × with ether. The aqueous phase was evaporated and the residue co-distilled with EtOH until dry. The dry residue was extracted with MeOH and 4 g of silica gel added. This was evaporated and the residue added to a 20 g silica gel (packed in CHCL$_3$) column. The column was washed with CHCl$_3$ and the product eluted with MeOH-CHCl$_3$ (10:90). The fractions were allowed to evaporate slowly. The crystals which formed after approximately ¼ volume had evaporated were filtered off and dried to give 40 mg of 59. The filtrate was evaporated to give an additional 262 mg of 59. Total yield 302 mg (13%): $\lambda_{max}^{pH\,1,\,11}$ 324 nm, 262 sh ($\epsilon$16,700, 14,200).

EXAMPLE 50

2-Amino-8-(p-chlorophenylthio)-6-piperidino-9-β-D-ribofuranosylpurine 3',5'-Cyclic Phosphate (60).

A solution of 2'-O-acetyl-2-amino-8-(p-chlorophenylthio)-6-chloro-9-β-D-ribofuranosylpurine 3',5'-cyclic phosphate sodium salt (59, 220 mg) in 10 ml of H$_2$O and 4 ml of piperidine was stirred overnight at room temperature. The solvent was evaporated, the residue was dissolved in water and acidified to pH 1 with 1 N HCl. The precipitate was filtered and recrystallized from 1:1 water: EtOH yield 120 mg.

Anal. Calcd for C$_{21}$H$_{24}$N$_6$O$_6$ClPS: C, 45.44; H, 4.35; N, 15.14. Found: C, 45.20; H, 4.44; N, 14.95.

Table 1

Uv Spectra and Tlc Mobility of 6,8-Disubstiuted-9-β-D-Ribofuranosylpurine 3',5'-Cyclic Phosphates

| Compound | X | Y | Z | Amax(nm)($\epsilon$×10$^{-3}$) pH 1 | pH 11 | RcAMP[a,b] A | B |
|---|---|---|---|---|---|---|---|
| 1a | OH | Br | COCH$_3$ | 252(14.7) | 257(13.4) | 2.00 | 2.00 |
| 1b | OH | Br | CO(CH$_2$)$_2$CH$_3$ | | | 2.75 | 2.20 |
| 2a | Cl | Cl | COCH$_3$ | 248(6.6),266(10.5), 274sh(8.8) | 248(6.6),266(10.2), 274sh(8.8) | 3.03 | 4.51 |
| 2b | Cl | Cl | CO(CH$_3$)$_2$CH$_3$ | | | 3.24 | 5.51 |
| 3 | NH$_2$ | Cl | | 259.5(15.6) | 261(14.3) | 1.50 | 1.63 |
| 4 | Cl | NH$_2$ | | 238(4.9),277(13.4) | 258(8.0),286(12.2) | 1.53 | 1.75 |
| 5 | Cl | OH | | 239(3.8),277(11.1) | 161(6.5),292(10.2) | 1.97 | 2.13 |
| 8-Cl-IMP[b,d] | OH | Cl | | 251 | 255 | 1.47 | 1.13 |
| 6 | SH | NH$_2$ | | 234(13.7),331(17.5), 297s(10.0) | 239(17.0),312(22.9) | 0.76 | 0.43 |
| S-SM-cAMP[b] | NH$_2$ | SH | | 244(13.4),308(25.2) | 291(22.4) | 1.86 | 1.14 |
| 7[d] | NEt$_2$ | OH | | 274,300sh | 290 | 2.54 | 2.38 |
| 8 | OH | OH | | 253(11.0),283sh(5.4) | 263(11.7) | 1.10 | 0.14 |
| 29 | SMe | SMe | | 246(13.7),309(16.5) 300 sh(14.5),330sh(11.6) | 245(15.6),307(22.2), 301sh(21.6) | 2.88 | 5.51 |
| 30 | NI-n-Butyl | Sme | | | | | |
| 32 | OH | S-p-ClPh | COCH$_3$ | 256(16.2),275sh(14.2) | 244(13.0),282(15.6) | 3.28 | 2.63 |
| 33 | Cl | S-p-ClPh | COCH$_3$ | 247(11.0),293(13.8) | 247(11.0),293(14.0) | 3.63 | 6.25 |
| 34 | Piperidine | S-p-ClPh | | 294(18.5) | 305(16.0) | 3.31 | 5.13 |
| 35 | Ni-n-Butyl | S-p-ClPh | | 286(20.7) | 293(18.0) | | |
| 37 | NHPh | S-p-ClPh | 298 | 309 | | | |
| 38 | NHCH(CH$_3$)C$_2$H$_5$ | S-p-ClPh | 287 | 293 | | | |
| 42 | NHCH$_2$Ph | Br | | 269(24.3) | 271(21.7) | 3.12 | 5.29 |
| 43 | NHCH$_2$Ph | SMe | 289(24.6) | 286(23.4) | 2.97 | 4.43 | |
| 44 | NHCH$_2$Ph | SCH$_2$Ph | | 289(20.6) | 290(18.3) | 3.30 | 5.00 |
| 45 | NHMe | SCH$_2$Ph | | 287(20.2) | 291(17.6) | 2.79 | 4.14 |
| 52 | MN-n-Butyl | Br | | 293(20.3) | 296(16.7) | | |

[a]RcAMP = mobility relative to that of cAMP in solvent systems A and B.
[b]Abbreviations used: cAMP, Adenosine 3',5'-cyclic phosphate; 8-Cl-cIMP, 8-Chloroinosine 3',5'-cyclic phosphate; 8-SH-cAMP, 8-Thioadenosine 3',5'-cyclic phosphate.
[c]R' = N unless otherwise indicated.
[d]Qualitative uv spectra only.

Table 2

PMR Spectra of Some Isomeric 6,8-Disubstituted and Related
6,8-Disubstituted 9-β-D-Ribofuranosylpurine 3',5'-Cyclic Phosphates[a,b,c]

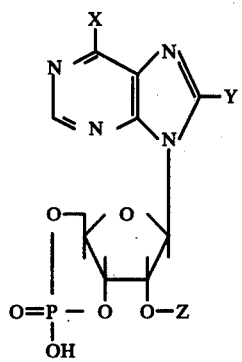

| Compound | X | Y | Z | $\delta,H_2$ | $\delta,H_1$ | $\delta,N(CH_2CH_3)_2$[d] | $\delta,N(CH_2CH_3)_2$[d] |
|---|---|---|---|---|---|---|---|
| 2 | Cl | Cl | COCH₃ | 8.95(s) | 6.21(s) | | |
| 3 | NH₂ | CL | H | 8.27(s) | 5.90(s) | | |
| 4 | Cl | NH₂ | H | 8.41(s) | 6.00(s) | | |
| 5 | Cl | OH | H | 8.51(s) | 5.75(s) | | |
| 8-Cl-cIMP[c] | OH | Cl | H | 8.21(s) | 5.86(s) | | |
| 6 | SH | NH₂ | H | 8.11(s) | 5.80(s) | | |
| 8-SH-cAMP[c] | NH₂ | SH | H | 8.24(s) | 6.54(s) | | |
| 9 | NEt₂ | Cl | H | 8.28(s) | 5.90(s) | 3.87(q) | 1.21(t) |
| 10 | Cl | NEt₂ | H | 8.55(s) | 5.70(s) | 3.49(q) | 1.24(t) |
| 11 | NEt₂ | NEt₂ | h | 8.17(s) | 5.74(s) | 3.91(q),3.25(q) | 1.21(t),1.12(t) |
| 15 | NEt₂ | SCH₂Ph | H | 8.26(s) | 5.84(s) | 3.95(m) | 1.24(t) |

[a]60 MHz spectra were determined on a Perkin Elmor 20A Spectrometer in DMSO-d₆.
[b]Proton chemical shifts in parts per million (δ) from internal DSS.
[c]Abbreviations used: s, singlet; t, triplet; q, quartet; m, multiplet; 8-Cl-cIMP, 8-chloroinosine 3',5'-cyclic phosphate; 8-SH-cAMP, 8-thioadenosine 3',5'-cyclic phosphate.
[d]Where applicable.

In the preceding examples of preferred embodiments of the invention, evaporations were performed in vacuo at <40°. UV spectra were determined on a Cary 15 spectrometer. Silica gel for column chromatography was E.M. Reagent Silica Gel 60 (particle size 0.063–0.200 mm). The eluates from column chromatography were monitored at 245 nm to detect the presence of uv absorbing compounds. Unless otherwise stated, analytical samples were dried at 80°–100° C. 0.01 mm for 12 hr. Tlc of the NH₄ salt of the compounds was run on E. Merck Silica Gel F-254 plates and developed with solvent system A CH₃CN:0.1M NH₄Cl (4:1) or B CH₃OH:CHCl₃(35:65). Elemental analyses were by Galbraith Laboratories, Inc., Knoxville, Tenn.

EXAMPLE 51

Compounds 12, 17, 19, 20, 24, 36, and 37 exhibit positive inotropic effect. Table 3 shows this effect as measured by the precent change in contractile force measured in isolated cat papillary muscle. Table 4 shows the in vivo positive inotropic effect of compound 12 measured in the intact anesthetized dog. The measurement dP/dT max was used as the index of change in myocardial contractility (inotropism). Compound 12 was given as an intravenous infusion at the rate of 1 mg/kg per min. in total single doses of 1.0 to 10.0 mg/kg and the values are expresses as percent of control. The same inotropic effect is seen in unanesthetized dogs as in anesthized dogs. In anesthetized dogs, compound 12 produces an increase in renal and mesenteric blood flow, effects which would be beneficial in treatment of cardiogenic shock.

Table 3

Positive Inotropic Effect

Figures indicate % change in Contractile Force (CF) measured in isolated cat papillary muscle

| Compound Number | X | Y | Concentration μg/ml | | | | | | |
|---|---|---|---|---|---|---|---|---|---|
| | | | 1.0 | 3.1 | 10.0 | 31.0 | 100 | 310 | 500 |
| 12 | N(Et)₂ | S-CH₂Ph | 3.8 % | 8.0 | 12.7 | 27.0 | 46.0 | 56.0 | |
| 17 | NH-n-Butyl | S-CH₂Ph | 7.5 | 10.0 | 19.3 | 24.0 | 30.0 | 39.0 | |
| 19 | NH-Et | S-CH₂Ph | 9.0 | 11.0 | 17.0 | 28.0 | 45.0 | 88 | |
| 20 | NH-n-Propyl | S-CH₂Ph | | | | | | 30 | 50 |
| 24 | NHCH₃ | S-CH₂Ph | 4.0 | 9.0 | 13.0 | 18.0 | 45.0 | 118.0 | |
| 36 | NH-n-Butyl | S-p-ClPh | 9.8 | 15.0 | 52.7 | 62.3 | 29.4 | 101.4 | |
| 37 | NHPh | S-p-ClPh | 2.0 | 10.3 | 31.3 | 50.2 | 74.5 | 82.3 | |

Table 4

| | | In Vivo Positive Inotropic Effect | | | | | |
|---|---|---|---|---|---|---|---|
| | | Measurement of myocardial contractility (inotropism) using dP/dT max (% of control) as index of measurement of inotropic effect. | | | | | |
| | | Time (minutes after infusion) | | | | | |
| | | Control | 1' | 3' | 5' | 15 | 30 |
| | 1.0 | 100% | 120% | 120% | 130% | 110% | |
| conc. of 12 mg/kg | 3.1 | 100% | 200% | 180% | 160% | 140% | 105% |
| | 10.0 | 100% | 210% | 200% | 180% | 140% | 100% |

Many of the compounds of the invention (e.g., compounds 4, 6, 9, 10, 11, 13, 14, 15, 16, 17, 18, 19, 34, 35, 42, 43, 44, and 56) inhibit phosphodiesterase markedly. Compounds 2a, 2b, 4, 9, 15-26, 30, 34-38, and 42-45 are superior to cyclic AMP from the standpoint of protein kinase activation, while compounds 2a, 2b, 11, and 16 inhibit adenyl cyclase function. Compounds 11 and 33 have displayed antihypertensive properties in in vivo animal testing, and in such testing compounds 16 and 33 have displayed anti-inflammatory activity.

The compounds of the invention may be provided in the 2'-O-acyl form by reaction with, e.g., $C_1$-$C_{18}$ (preferably $C_1$-$C_7$) acid anhydrides or acid halides in base. The acyl group can be selected from a group consisting of straight chain, branched chain, substituted, unsaturated, saturated, or aromatic acid such as, but not necessarily limited to, acetic, trifluoracetic, propionic, n-butyric, isobutyric, valeric, caproic, pelargonic, enanthic, caprylic, latic, acrylic, propargylic, palmitic, benzoic, phthalic, salicyclic, cinnamic, and naphthoic acids. Sutherland et al, Biochem. et Biophys. Acta 148, 106 (1967) have demonstrated that acylation of cyclic AMP enhances cellular transport of the purine nucleotide.

The compounds of the invention may optionally be provided as additional salts of either the cyclic phosphate moiety or any basic moiety, e.g., 6-substituted amino compounds, or they may exist as a zwitterionic compound.

Acceptable acid additional salts of the basic moiety can be selected from, but not necessarily limited to, the group consisting of hydrochloride, hydrobromide, hydroiodide, citrate, sulfate, substituted sulfate, phosphate, carbonate, bicarbonate, and formate. Acceptable salts of the phosphate moiety can be selected from, but not necessarily limited to, the group consisting of alkali and alkaline earths, e.g., sodium, potassium, calcium, magnesium, lithium, ammonium and substituted ammonium, trialkylammonium, dialkylammonium, alkylammonium, e.g., triethylammonium, trimethylammonium, diethylammonium, octylammonium, cetyltrimethylammonium, cetylpyridium.

We claim:

1. A compound of the structure:

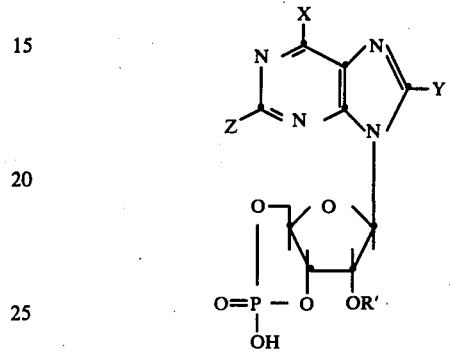

wherein Z is hydrogen or —$NH_2$; R' is hydrogen or $C_1$-$C_{18}$ acyl; X is $NR_1R_2$, Cl, Br, or $SR_3$; Y is $SR_4$; $R_1$ and $R_2$ are independently selected from the group consisting of hydrogen, phenyl, $C_7$ to $C_{10}$ aralkyl, saturated or unsaturated straight or branched chain $C_1$ to $C_7$ alkyl, or $R_1$ and $R_2$ are lower alkyl joined together to form a pyrrolidino or piperidino ring; $R_3$ is hydrogen, lower alkyl, phenyl, or benzyl; and $R_4$ is phenyl, $C_7$ to $C_{10}$ aralky, or substituted phenyl and substituted $C_7$ to $C_{10}$ aralkyl wherein the substituents are selected from the group consisting of chloro, bromo, fluoro, methyl, methoxy, or nitro, with the proviso that when one of $R_1$ or $R_2$ is hydrogen the other is not.

2. A compound according to claim 1 wherein X is $NR_1R_2$; Y is $SR_4$; $R_1$ and $R_2$ are independently selected from the group consisting of hydrogen, phenyl, $C_7$ to $C_{10}$ aralkyl, saturated or unsaturated straight or branched chain $C_1$ to $C_7$ alkyl, or $R_1$ and $R_2$ are lower alkyl joined together to form a pyrrolidino or piperidion ring; $R_4$ is phenyl, $C_7$ to $C_{10}$ aralkyl or substituted phenyl and substituted $C_7$ to $C_{10}$ aralkyl wherein the substituents are selected from the group consisting of chloro, bromo, fluoro, methyl, methoxy, or nitro, with the proviso that when one of $R_1$ or $R_2$ is hydrogen the other is not.

3. A compound according to claim 2 wherein Z is hydrogen and R' is hydrogen.

4. A compound according to claim 2 wherein $R_1$ and $R_2$ are independently selected from the group consisting of hydrogen, methyl, ethyl, n-propyl, iso-propyl, n-butyl, sec-butyl, iso-butyl, n-pentyl, iso-pentyl, neo-pentyl, or n-hexyl; and $R_4$ is phenyl, p-chlorophenyl, or benzyl.

5. A compound according to claim 2 wherein $R_4$ is phenyl, benzyl, or substituted phenyl and substituted benzyl and the substituents are selected from the group consisting of chloro, bromo, fluoro, methyl, methoxy, or nitro.

6. A compound according to claim 2 wherein Z is hydrogen; R' is hydrogen; X is selected from the group consisting of methylamino, ethylamino, n-propylamino, n-butylamino, n-pentylamino, n-hexylamino; and Y is benzylthio, phenylthio, or p-chlorophenylthio.

7. A compound according to claim 4 designated 8-benzylthio-6-dimethylamino-9-β-D-ribofuranosylpurine 3′,5′-cyclic phosphate.

8. A compound according to claim 4 designated 8-benzylthio-6-diethylamino-9-β-D-ribofuranosylpurine 3′, 5′-cyclic phosphate.

9. A compound according to claim 4 designated 8-benzylthio-6-dipropylamino-9-β-D-ribofuranosylpurine 3′,5′-cyclic phosphate.

10. A compound according to claim 4 designated 8-benzylamino-6-n-pentylamino-9-β-D-ribofuranosypurine 3′,5′-cyclic phosphate.

11. A compound according to claim 4 designated 8-benzylthio-6-n-hexylamino-9-βD-ribofuranosylpurine 3′,5′-cyclic phosphate.

12. A compound according to claim 4 designated 8-benzylthio-6-methylbutylamino-9-β-D-ribofuranosylpyrine 3′,5′-cyclic phosphate.

13. A compound according to claim 4 designated 8-benzylthio-6-iso-propylamino-9-β-D-ribofuranosylpurine 3′, 5′-cyclic phosphate.

14. 8-Benzylthio-6-methylamino-9-β-D-ribofuranosylpurine 3′,5′-cyclic phosphate.

15. 8-Benzylthio-6-ethylamino-9β-D-ribofuranosylpurine 3′,5′-cyclic phosphate.

16. 8-Benzylthio-6-n-propylamino-9-β-D-ribofuranosylpurine 3′,5′-cyclic phosphate.

17. 8-Benzylthio-6-n-butylamino-9-β-D-ribofuranosylpurine 3′,5′-cyclic phosphate.

* * * * *